(12) United States Patent
Kim et al.

(10) Patent No.: US 6,635,040 B1
(45) Date of Patent: Oct. 21, 2003

(54) ELASTIC SIDED ABSORBENT PAD WITH SOFT COMFORTABLE SIDE PANELS

(75) Inventors: Doo-Hong Kim, Kyunggi (KR); Hyung-Bum Kim, Kyunggi (KR); Eo-Yeon Hwang, Kyunggi (KR); Eun-Jung Kang, Seoul (KR)

(73) Assignee: Yuhan-Kimberly Ltd., Seoul (KR)

( * ) Notice: Subject to any disclaimer, the term of this patent is extended or adjusted under 35 U.S.C. 154(b) by 0 days.

(21) Appl. No.: 09/744,556

(22) PCT Filed: Aug. 9, 1999

(86) PCT No.: PCT/KR99/00441

§ 371 (c)(1), (2), (4) Date: Jan. 24, 2001

(87) PCT Pub. No.: WO00/09056

PCT Pub. Date: Feb. 24, 2000

(30) Foreign Application Priority Data

Aug. 10, 1998 (KR) .............................. 98-32388

(51) Int. Cl.⁷ ................................................ A61F 13/15
(52) U.S. Cl. ............................ 604/385.04; 604/385.24; 604/387
(58) Field of Search .................. 604/378, 379, 604/380, 385.01, 385.03, 385.04, 385.21, 385.23, 385.24, 385.25, 385.27, 387; A61F 13/15

(56) References Cited

U.S. PATENT DOCUMENTS

| | | | |
|---|---|---|---|
| 4,397,645 A | 8/1983 | Buell | |
| 4,655,759 A | 4/1987 | Romans-Hess et al. | |
| 4,701,177 A | 10/1987 | Ellis et al. | |
| 4,770,657 A | * 9/1988 | Ellis et al. | 604/370 |
| 4,857,067 A | 8/1989 | Wood et al. | |
| 4,938,757 A | 7/1990 | Van Gompel et al. | |
| 4,940,462 A | * 7/1990 | Salerno | 604/385.04 |
| 4,944,735 A | 7/1990 | Mokry | |
| 5,032,121 A | 7/1991 | Mokry | |
| 5,074,856 A | * 12/1991 | Coe et al. | 604/370 |
| 5,171,302 A | 12/1992 | Buell | |
| 5,234,422 A | 8/1993 | Sneller et al. | |
| 5,308,346 A | 5/1994 | Sneller et al. | |
| 5,397,318 A | 3/1995 | Dreier | |
| 5,486,167 A | * 1/1996 | Dragoo et al. | 604/358 |
| 5,542,941 A | 8/1996 | Morita | |
| 5,704,928 A | * 1/1998 | Morita et al. | 604/385.04 |
| 5,807,363 A | * 9/1998 | Hamajima et al. | 604/366 |
| 5,891,121 A | * 4/1999 | Redwine et al. | 604/387 |
| 6,316,688 B1 | * 11/2001 | Hammons et al. | 604/378 |

FOREIGN PATENT DOCUMENTS

| | | |
|---|---|---|
| EP | 534488 A1 | 3/1993 |
| EP | 590675 B1 | 5/1997 |
| EP | 595047 B1 | 5/1997 |
| EP | 0 596 532 B1 | 7/1998 |
| WO | WO 91/18573 | 12/1991 |
| WO | WO93/10733 | 6/1993 |

OTHER PUBLICATIONS

International Search Report for PCT/KR 99/00441.

* cited by examiner

*Primary Examiner*—Weilun Lo
*Assistant Examiner*—Jamisue A. Webb
(74) *Attorney, Agent, or Firm*—Senniger, Powers, Leavitt & Roedel

(57) ABSTRACT

An elastic sided curved absorbent pad is provided with soft side edges providing efficient leakage protection without irritation. The pad has elasticized side panels which comprise at least two layers of non-woven material mounted between a cover and baffle, projecting beyond the side edges of the cover and the baffle, giving the panel soft, free outer distal edges and one or more elastic members inboard from the free distal edge. The layers of non-woven material and the elastic member are bonded together, except for the distal edges which are not bonded. This provides a lace-like appearance and feel.

23 Claims, 3 Drawing Sheets

ELASTIC SIDED ABSORBENT PAD WITH SOFT COMFORTABLE SIDE PANELS

BACKGROUND OF THE INVENTION

This invention relates to an absorbent pad, such as a feminine pad, sometimes called a sanitary napkin, or an adult incontinence pad. More specifically, this invention relates to an absorbent pad having elasticized side panels comprising at least two layers of non-woven material mounted between a liquid pervious topsheet or cover and a liquid impervious backsheet or baffle. The elasticized side panels project beyond side edges of the cover and the baffle, giving the panel free outer distal edges. The layers of non-woven material are bonded together by at least one elastic member positioned inboard from the free distal edge. The distal edges of the side panels are not bonded together thereby providing a lace-like appearance and feeling.

In most absorbent pads, such as feminine pads and incontinence pads manufactured today, the side edges of the pads are closer to the fluid discharge area than the front and back edges of the pad. Thus, the pads tend to leak at the side edges rather than at the front and back edges. It is common for body fluid deposited onto the cover to pool before it penetrates down through the fluid-permeable cover and into an absorbent core. Side leakage occurs when the deposited body fluid pools on the cover material and spreads along the surface of the cover to the edges before being absorbed into the absorbent core.

Attempts have been made to reduce side leakage by providing side panels or flaps extending outward from and along the side edges of the pad. European Patent Application 0,534,488 A1 to Menard relates to a pad having elasticized side panels formed by a sheet which wraps around the side edges of the pad. PCT WO 93/10733 to Morita discloses a pad having elasticized side panels formed by portions of the backsheet and/or the topsheet which wrap around the side edges of the pad.

U.S. Pat. No. 5,542,941 to Morita discloses a pad having elasticized side panels formed by material wrapped around the side edges of the pad.

U.S. Pat. Nos. 5,234,422 and 5,308,346 to Sneller disclose a sanitary napkin having elasticized side panels. In one embodiment, the elastic members associated with the side flaps are wrapped around the side edges of the pad. In another embodiment of the Sneller patent, the elastic members extend laterally outward beyond the distal edges of the baffle and cover. The elastic members comprise an elastomeric laminate such as a three layer laminate comprising a coverstock layer, a second coverstock layer and an elastomeric layer, such as an elastomeric film, positioned between and operatively associated with the coverstock layers.

Other patents, which teach various aspects of absorbent pads, include: U.S. Pat. No. 5,397,318 to Dreier, U.S. Pat. Nos. 4,770,657 and 4,701,177 to Ellis et al., U.S. Pat. Nos. 5,171,302 and 4,397,645 to Buell, U.S. Pat. No. 5,032,121 and 4,944,735 to Mokry, U.S. Pat. No. 4,938,757 to Van Gompel et al., U.S. Pat. No. 4,655,759 to Romans-Hess et al., U.S. Pat. No. 5,074,856 to Coe et al., and European Patent Applications 0 590 675 and 0 595 047 to Van Gompel et al.

The foregoing elastic-sided pads have a curved shape which prevents side leakage of body fluid and conforms to the curved shape of a human crotch. Through the present invention, a comfortable sanitary napkin having soft side edges and efficient leakage protection is provided.

SUMMARY OF THE INVENTION

Briefly, this invention relates to a curved and elastic-sided absorbent pad, such as a feminine pad sometimes called a sanitary napkin or an adult incontinence pad, having exceptionally soft and aesthetically pleasing side panels. The elasticized side panels have lace-like soft edges and bias the pad into a curved configuration when unfolded. The side panels include at least two layers of a non-woven material mounted between the cover and baffle, and the distal edges of the layers extend outward beyond the side edges of the cover and the baffle. Elastics are provided on the non-woven materials, but they are positioned inboard from the outer distal edges and the layers are not bonded together at their free edges to provide soft, comfortable and non-irritating edges.

DETAILED DESCRIPTION OF THE INVENTION

Figure 1:
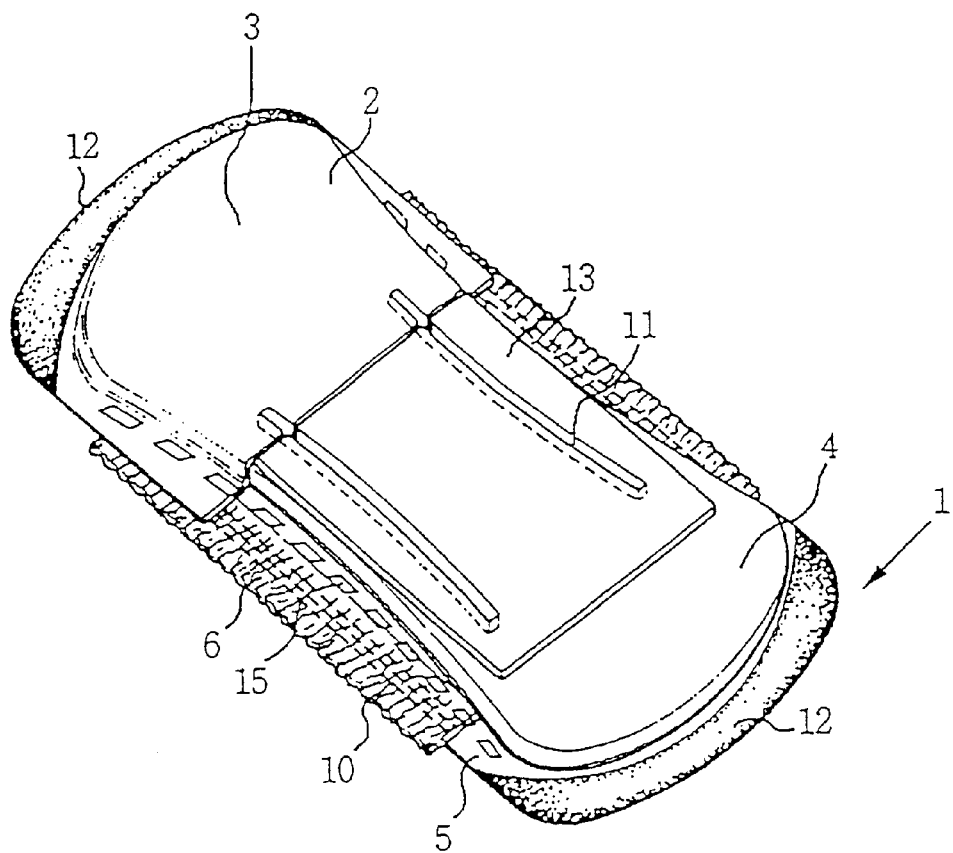
FIG. 1 is a perspective cut-away view of an absorbent pad having lace-like elasticized side panels.
Figure 2:
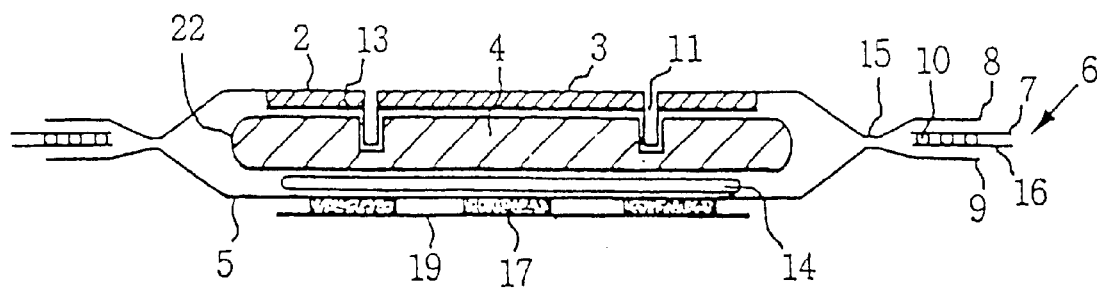
FIG. 2 is an endwise cross-sectional schematic view of the pad taken along a line extending laterally across the pad midway along its length.
Figure 3:
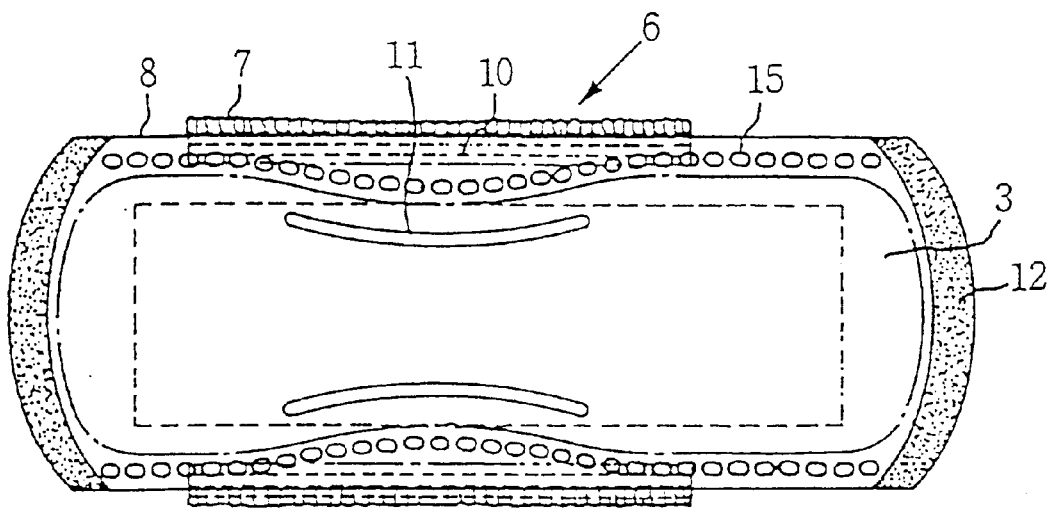
FIG. 3 is a top plan view of the pad showing a cover.

Referring to FIGS. 1 and 2, an absorbent pad, such as a feminine pad or adult incontinence pad, is designated in its entirety by the reference numeral 1. The pad 1 is designed to be worn by a female or adult to adsorb body fluids such as menses, blood, urine, and other excreta. The pad 1 comprises has a liquid-permeable cover 2 having a bodyside surface 3, an absorbent core 4, a breathable plastic baffle 5 and shirred or gathered elasticized side panels 6. As illustrated in FIG. 2, the side panels 6 are formed from at least two layers 16 of a non-woven material mounted between the cover 2 and the baffle 5, and have outer distal edges 7 which project at least one millimeter beyond side edges 8, 9 of the cover 2 and the baffle 5. Elastic members 10 are positioned on or between the non-woven layers 16 and inboard from the outer distal edges 7 of the side panels 6.

The liquid-permeable cover 2 may be made of apertured film, non-woven fabric or a laminate comprising both apertured film and non-woven fabric. One such laminate comprises an apertured film and a through air bonded carded non-woven fabric bonded together by a point-to-point bonding process in a desired pattern. A process for making the laminate is described in European Patent Application EP 0 596 532 to Alikhan. In one embodiment, the cover 2 is 20 grams per square meter (gsm) and air permeable.

The cover 2 and the baffle 5 may be aligned and bonded together so they have non-bonded soft free distal edges. This is achieved by bonding the margins of the cover 2 and baffle 5 adjacent the side edges 8, 9 but not bonding portions of the cover and baffle immediately adjacent the distal edges. The portions of the cover 2 and baffle 5 which are not bonded are at least about 0.5 millimeter wide and extend inward from the very ends of the side edges 8, 9, thereby forming free distal edges. After bonding, the side edges 8,9 are not cut.

Figure 5:
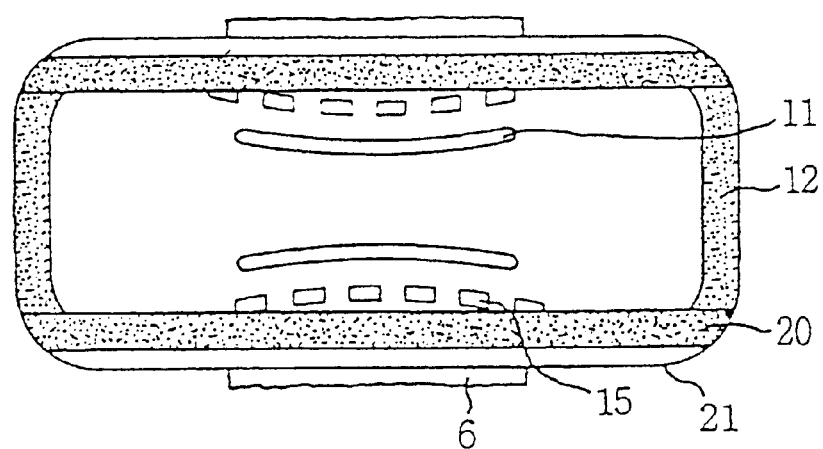
FIG. 5 is a top plan view of a pad of a second embodiment.

Alternatively, the cover 2 may be folded toward the bodyside surface 3 as shown in FIG. 5. The folded portions 20 of the cover 2 are bonded to the corresponding portions of the bodyside surface 3 of the cover by point-heat sealing or adhesive, except at the very distal ends 21 of the side edges of the baffle 5. In this alternate embodiment, the side margins of the cover 2 and the baffle 5 are also bonded, except for a portion no less than about 0.5 millimeter from the very ends 21 of the side edges 8, 9 which are not bonded together, thereby forming free distal edges. The non-bonded distal ends 21 provide a cushioning effect and a neat appearance.

The liquid-permeable cover 2 may have a plurality of apertures (not shown) formed therein arranged along the longitudinal centerline, if desired. The apertures increase the rate at which body fluids penetrate down into the absorbent core 4. The cover 2 may also be treated with a surfactant to increase its hydrophilic properties. The surfactant may consist of surface applied materials or internally applied materials such as polysiloxanes.

The moisture-impervious baffle 5 is generally vapor and air permeable while blocking the passage of body fluids and other liquids. In one embodiment, the baffle 5 is formed of polyethylene film-laminated non-woven materials which feel like natural textile. Further, the baffle 5 of this embodiment is about 45 grams per square meter, dimple embossed, and has a water vapor transfer rate (WVTR) of about 1,000 grams per cubic centimeter per day (g/cc/day) to about 4000 g/cc/day. The baffle 5 may contain a filler and may be stretched to achieve better vapor permeability.

In one embodiment, the cover 2 and the baffle 5 are approximately rectangular, and do not have an hourglass shape. The cover 2 and baffle 5 may extend beyond the side edges 22 of the absorbent core 4.

The absorbent core 4 may be secured to the baffle 5 by an adhesive or, alternatively, it may be enclosed by a liquid permeable cover (not shown). In one embodiment, the absorbent core 4 has an hourglass shape. In one embodiment, the absorbent core 4 extends laterally across at least about 50% of the pad 1, desirably at least about 75% of the pad, and more desirably extends essentially across the entire width of the pad and terminates at seal lines extending along the side margins of the cover 2 and baffle 5. The absorbent core 4 has the capability of absorbing essentially the entire amount of body fluid deposited onto the pad. The absorbent core 4 can be composed of traditional fluff, coform, air-laid tissue, uncreped through air-dried toweling, staple fibers, conventional tissue and the like. In one embodiment, the core 4 has no embossing pattern. Superabsorbents are also very good at retaining body fluids, absorbing a great amount of fluid in relation to their own weight. Typical superabsorbents used in feminine pads may be used in the core 4.

The elastic side panel or side elastic 6 is composed of polypropylene/polyethylene non-woven elastic material. In one embodiment, the side elastic 6 is a non-woven material which is hydrophobic and more than about 15 gsm. Further, the material of this embodiment is a through air bonded carded web. To prevent irritation which may occur from lamination, the non-woven material has low fiber density, less than about 0.036 gram per cubic centimeter (g/cc), and desirably less than about 0.018 g/cc. In one embodiment, the side panels 6 comprise at least two layers of non-woven material of low fiber density and at least one elastic member which is positioned inboard from the distal free edges of the layers or non-woven material. In particular, the layers non-woven material and the elastic member of this embodiment are bonded together by an adhesive, except for portions no less than about 0.5 millimeter from the very end of the distal edges 7 of the side panels 6 which are not bonded. At least one elastic member or strand 10 is positioned on or between the layers of non-woven carrier sheet material 16, thereby forming a loosely laminated lace of a certain elasticity and size.

The loosely-laminated, elastic lace may be a laminated material comprising through air bonded carded web and Lycra (trademark of E. I. du Pont de Nemours and Company) filaments or nonwoven and elastic threads. In one embodiment, the elastic strand 10 is made of Lycra filaments and has a weight of about 560 denier about 840 denier. It usually is stretched to a length between about 120% and about 200% of its unstretched length. Elastic members 10 may be tensioned and spaced from the absorbent core 4 to cause the side panels 6 to curl upward out of plane from the core to improve side leakage protection of the pad 1.

In one embodiment, the bodyside surface 3 of the pad 1 has two arcuate embossed lines 11 (also called channels, side stoppers or fluff fasteners). The embossed lines 11 increase the density of the absorbent core 4 and increase the resistance of the pad 1 to bunching and cover swell during use. They also prevent side leakage.

Optionally, a surge or acquisition layer 13 may be positioned between the cover 2 and the absorbent core 4 to prevent rewetting and ensure absorbency. The surge layer 13 is made of non-woven material composed of polyester fiber and a two component fiber made from polypropylene and polyethylene or the material may be an air-laid, through air bonded carded web or a thermal bonded carded web. The surge layer 13 is usually rectangular and is bonded to the cover 2, e.g., in a honeycomb pattern.

An integrity tissue 14 is optionally positioned between the absorbent core 4 and the baffle 5. The integrity tissue 14 is positioned to constrain the absorbent core 4 that is, to prevent separation or coagulation. The integrity tissue 14 of one embodiment has an hourglass shape, is about 35 gsm and can be air-laid or fluff.

Figure 6:
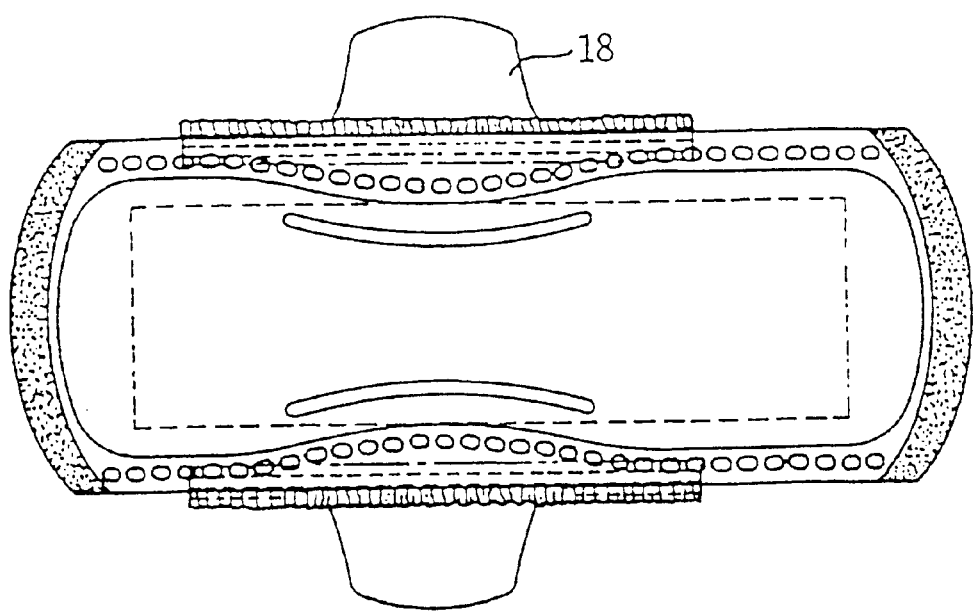
FIG. 6 is a top plan view of a pad of a third embodiment having tabs.

In one embodiment, the pad 1 has an hour-glass shape with wide end radii, thereby preventing end leakage and providing a more stable and closer contact with the body. The pad 1 also may include tab 18 as shown in FIG. 6. A portion of each tab that is bonded to the baffle 5 may be positioned between the side panel 6 and the baffle 5 or alternatively adjacent the baffle on a surface opposite the side panel.

In one embodiment of the pad 1 for a normal amount of menstruation, the pad is about 220 millimeters (mm) to about 250 mm long and about 100 millimeters wide. The absorbent core 4 is about 230 mm long and about 65 to about 85 mm wide. The surge (or acquisition layer) 13 is about 230 mm long and about 55 mm wide. The integrity tissue 14 is about 130 mm long. The side panel 6 is about 160 mm long when stretched to about 150% of its unstretched length.

The cover 2 and the baffle 5 are bonded together at the sides 15, e.g., by point-heat sealing with adhesive and at the ends 12, e.g., by patterned-heat sealing. Alternatively, the cover 2 and baffle 5 are bonded by peripheral two-line heat sealing with adhesive to provide a neat, clean treatment and prevent irritation.

Figure 4:
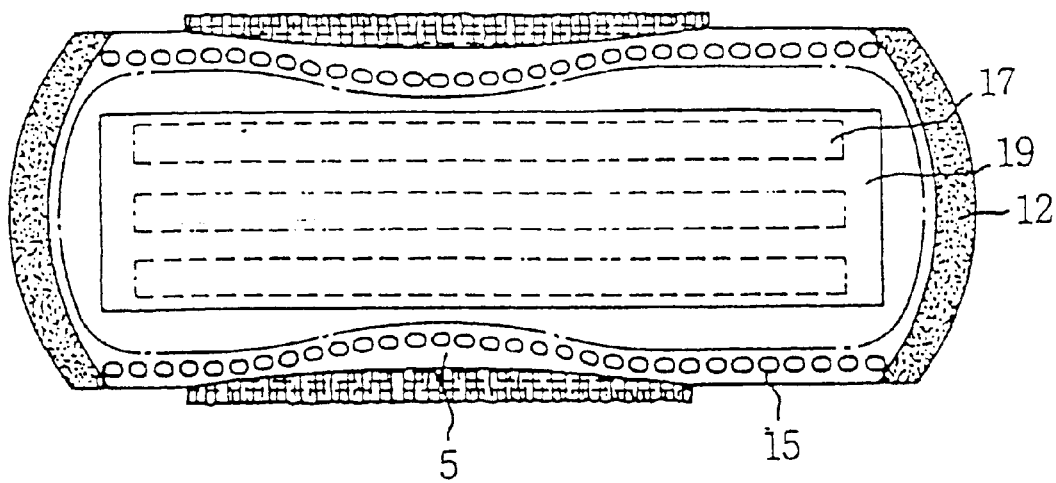
FIG. 4 is a bottom plan view of the pad showing a baffle.

Referring to FIGS. 2 and 4, an adhesive 17 may be placed on the baffle 5 in any desired arrangement including a series of narrow strips for holding the pad 1 in position in a garment (not shown). One arrangement has the adhesive formed in one strip. A peel strip 19 covers the adhesive 17. In one embodiment, the peel strip 19 has a total width of about 1 inch to about 1½ inches (2.54 to 3.81 centimeters) and a length of about 4 to about 6 inches (10.16 to 15.24 centimeters). The adhesives 17 may include hot-melt adhesives. The garment adhesive may also have three lines of paper tapes or peel strips 19 having a length of about 210 mm, a width of about 10 mm and weighing about 0.32 grams. Lines of adhesives 17 are desirably spaced about 9.55 mm apart from each other.

EXAMPLE 1

A feminine pad for a heavy menstruation period could have the following configuration:

|  | length (mm) | width (mm) | weight (g) | bulk (mm) | shape |
|---|---|---|---|---|---|
| fluff | 254 | 65 (c) 80 (e) | 8.43 | 6.5 | hourglass |
| cover | 282 | 100 | 0.54 |  |  |
| surge | 210 | 65 (c) | 0.41 |  | rectangular |
| baffle | 282 | 98 | 1.20 |  |  |
| integrity tissue | 254 | 65 (c) 80 (e) | 0.65 |  | hourglass |
| elasticized side panels (see Example 2) |  |  |  |  |  |
| garment adhesive | 210 | 10 (each) | 0.32 50.7 gsm |  |  |
| peel strip | 230 | 55 | 0.76 |  |  |
| finished pad | 282 | 110 | 12.99 |  |  |

EXAMPLE 2

In the pad of Example 1, the elasticized side panels, desirably of Lycra laminates, have the following structure:

| Lycra laminate | |
|---|---|
| length (relaxed) | 135 mm |
| length (under tension) | 150 mm |
| width/side | 12 mm |
| Lycra strand/side | 3 |
| wherein, the Lycra strand has the following structure: | |
| length (relaxed) | 135 mm |
| stretch after lamination | 125% |
| weight (both sides) | 0.07 g |
| the layer of nonwoven material has the following structure: | |
| length | 168 mm |
| width/side | 12 mm |
| weight (both sides) | 0.039 g |

While the invention has been described in conjunction with several specific embodiments, it is to be understood that many alternatives, modifications and variations will be apparent to those skilled in the art in light of the foregoing description. Accordingly, this invention is intended to embrace all such alternatives, modifications and variations which fall within the spirit and scope of the appended claims.

What is claimed is:

1. An elastic-sided absorbent pad comprising:

a) a liquid permeable cover having a bodyside surface, an absorbent-core-side surface opposite said bodyside surface, opposite front and back ends and opposite side edge margins extending to respective side edges;

b) a liquid impermeable baffle having an absorbent-core-side surface, a garment-side surface opposite said absorbent-core-side surface, opposite front and back ends and opposite side edge margins extending to respective side edges, wherein the side edge margins of said cover and said baffle are bonded except for portions within at least about 0.5 millimeter of said respective side edges thereby forming free distal edges;

c) an absorbent core positioned between the cover and the baffle, said absorbent core having a pair of side edges;

d) a pair of shirred elasticized side panels, each operatively positioned between the cover and the baffle, extending outwardly from and along each side edge of said absorbent core and projecting at least about one millimeter beyond the respective side edge margins of the cover and the baffle thereby having a free distal edge, each elasticized side panel comprising at least two layers of non-woven material having a fiber density less than about 0.036 gram per cubic centimeter and at least one elastic member positioned inboard from the free distal edge of the respective panel, wherein said layers of non-woven material and said elastic member are bonded together, except for a portion within at least about 0.5 millimeter of said free distal edge of the respective panel which is not bonded.

2. An elastic-sided absorbent pad as set forth in claim 1 wherein said layers of non-woven material of said elasticized side panels has density of less than about 0.018 gram per cubic centimeter.

3. An elastic-sided absorbent pad as set forth in claim 1 wherein each of said elasticized side panels comprises a polypropylene/polyethylene non-woven elastic material.

4. An elastic-sided absorbent pad as set forth in claim 1 wherein each of said elasticized side panels comprises a hydrophobic non-woven material having a weight per unit area of more than about 15 grams per square meter.

5. An elastic-sided absorbent pad as set forth in claim 1 wherein said elastic member is stretched to a length which is between about 120% and about 200% of its unstretched length.

6. An elastic-sided absorbent pad as set forth in claim 1 wherein said bodyside surface of the cover has least two embossed lines extending from the cover into the absorbent core.

7. An elastic-sided absorbent pad as set forth in claim 1 further comprising a surge comprising a non-woven material positioned between the cover and the absorbent core.

8. An elastic-sided absorbent pad set forth in claim 1 further comprising an integrity tissue positioned between the absorbent core and the baffle.

9. An elastic-sided absorbent pad as set forth in claim 1 wherein the absorbent core has an hourglass shape and the cover and the baffle extend laterally beyond the side edges of the absorbent core.

10. An elastic-sided absorbent pad as set forth in claim 1 wherein the pad further comprises at least one line of garment adhesive extending longitudinally along the pad.

11. An elastic-sided absorbent pad as set forth in claim 1 wherein the pad further comprises a wing extending laterally with respect to the cover.

12. An absorbent pad comprising:

a liquid permeable cover having a bodyside surface, an absorbent-core-side surface opposite said bodyside surface and opposite side edge margins extending to respective side edges of the cover, each of said side edge margins of the cover having an inboard portion spaced at least about 0.5 millimeter from the respective side edge of the cover and an outboard portion extending from the corresponding inboard portion to the respective side edge of the cover;

a liquid impermeable baffle having an absorbent-core-side surface facing the absorbent-core-side surface of the cover, a garment-side surface opposite said absorbent-core-side surface and opposite side edge margins extending to respective side edges of the baffle, each of said side edge margins of the baffle having an inboard portion spaced at least about 0.5 millimeter from the respective side edge of the baffle and an outboard portion extending from the corresponding inboard portion to the respective side edge of the baffle;

the inboard portion of each side edge margin of said cover bonded to the corresponding inboard portion of each side edge margin of said baffle;

the outboard portion of each side edge margin of said cover substantially free from the corresponding outboard portion of each side edge margin of said baffle;

an absorbent core positioned between the absorbent-core-side surface of the cover and the absorbent-core-side surface of the baffle; and a pair of side panels, each of said side panel at least partially received between the cover and the baffle along respective side edge margins thereof and extending outward from and projecting at least about one millimeter beyond the respective side edges of the cover and the baffle, the side panels each having opposite ends, the cover and the baffle bonded substantially continuously along a region extending between respective ends of the side panels, the bond at said region free of any intermediate connection to the side panels.

13. An absorbent pad as set forth in claim 12 wherein the absorbent core has an hourglass shape and the cover and the baffle extend laterally beyond side edges of the absorbent core.

14. An absorbent pad as set forth in claim 12 wherein the pad further comprises at least one line of garment adhesive extending longitudinally along the pad.

15. An absorbent pad as set forth in claim 12 wherein the pad further comprises a wing extending laterally with respect to the cover.

16. An absorbent pad as set forth in claim 12 wherein each side panel comprises at least two layers of non-woven material having a fiber density less than about 0.036 gram per cubic centimeter and at least one elastic member, wherein said layers of non-woven material and said elastic member are bonded together.

17. An absorbent pad as set forth in claim 16 wherein said layers of non-woven material of said side panels has density of less than about 0.018 gram per cubic centimeter.

18. An absorbent pad as set forth in claim 16 wherein each of said side panels comprises a polypropylene/polyethylene non-woven elastic material.

19. An absorbent pad as set forth in claim 16 wherein each of said side panels comprises a hydrophobic non-woven material having a weight per unit area of more than about 15 grams per square meter.

20. An absorbent pad as set forth in claim 16 wherein said elastic member is stretched to a length which is between about 120% and about 200% of its unstretched length.

21. An absorbent pad as set forth in claim 12 wherein said bodyside surface of the cover has at least two embossed lines extending from the cover into the absorbent core.

22. An absorbent pad as set forth in claim 12 further comprising a surge comprising a non-woven material positioned between the cover and the absorbent core.

23. An absorbent pad as set forth in claim 22 further comprising an integrity tissue positioned between the absorbent core and the baffle.

* * * * *

UNITED STATES PATENT AND TRADEMARK OFFICE
CERTIFICATE OF CORRECTION

PATENT NO. : 6,635,040 B1  Page 1 of 1
DATED : October 21, 2003
INVENTOR(S) : Kim et al.

It is certified that error appears in the above-identified patent and that said Letters Patent is hereby corrected as shown below:

Column 2,
Line 38, "adsorb" should read -- absorb --.
Line 40, "comprises has a" should read -- comprises a --.

Column 4,
Line 14, "denier about" should read -- denier to about --.
Line 45, "tab" should read -- tabs --.

Column 5,
Line 48, "the layer" should read -- and the layer --.

Signed and Sealed this

Fifteenth Day of June, 2004

JON W. DUDAS
*Acting Director of the United States Patent and Trademark Office*